US008609135B2

(12) United States Patent
Edwards et al.

(10) Patent No.: US 8,609,135 B2
(45) Date of Patent: Dec. 17, 2013

(54) ANTHRACYCLINE DERIVATIVES (75) Inventors: Katarina Edwards, Uppsala (SE); Stefan Sjöberg, Uppsala (SE); Jörgen Carlsson, Uppsala (SE); Lars Gedda, Uppsala (SE)

(73) Assignee: Nuclisome AB, Uppsala (SE)

( * ) Notice: Subject to any disclaimer, the term of this patent is extended or adjusted under 35 U.S.C. 154(b) by 385 days.

(21) Appl. No.: 12/578,380

(22) Filed: Oct. 13, 2009

(65) Prior Publication Data

US 2010/0092388 A1 Apr. 15, 2010

Related U.S. Application Data (62) Division of application No. 11/578,159, filed as application No. PCT/SE2005/000596 on Apr. 22, 2005, now abandoned.

(30) Foreign Application Priority Data

Apr. 22, 2004 (SE) ...................................... 0401066

(51) Int. Cl.
*A61K 9/127* (2006.01)
*A01N 43/04* (2006.01)
*A61K 31/70* (2006.01)
*C07H 15/24* (2006.01)

(52) U.S. Cl.
USPC ............................. 424/450; 514/34; 536/6.4

(58) Field of Classification Search
None
See application file for complete search history.

(56) References Cited

U.S. PATENT DOCUMENTS

| 4,177,264 | A | 12/1979 | Wu et al. |
| 4,250,303 | A | 2/1981 | Wu et al. |
| 4,526,960 | A | 7/1985 | Broadhurst et al. |
| 4,610,977 | A | 9/1986 | Israel et al. |
| 4,948,880 | A | 8/1990 | Hermentin et al. |
| 5,003,055 | A | 3/1991 | Takeuchi et al. |
| 5,874,412 | A | 2/1999 | Priebe et al. |
| 6,673,907 | B2 | 1/2004 | Priebe et al. |
| 2002/0137694 | A1* | 9/2002 | Priebe et al. ..................... 514/34 |
| 2005/0004048 | A1 | 1/2005 | Priebe et al. |

FOREIGN PATENT DOCUMENTS

| JP | 53-9756 A | 1/1978 |
| WO | 03/057687 A1 | 7/2003 |

OTHER PUBLICATIONS

Dorwald (Side Reactions in Organic Synthesis: A Guide to Successful Synthesis Design, Weinheim: WILEY-VCH Verlag GmbH & Co. KGaA, 2005, Preface).*
Leenders et al. (Bioorganic & Medicinal Chemistry Letters, vol. 5, No. 24, pp. 2975-2980, 1995).*
O'Donoghue et al. (Phys. Med. Biol. 1973-1992, 1996).*
Hope et al, "Production of large unilamellar vesicles by a rapid extrusion procedure. Characterization of size distribution, trapped volume and ability to maintain a membrane potential", Biochimica et Biophysica Acta, 812 (1985) pp. 55-65.
Gaze, "The current status of targeted radiotherapy in clinical practice", Phys. Med. Biol., 41 (1996) pp. 1895-1903.
O'Donoghue et al, "Targeted radiotherapy using Auger electron emitters", Phys. Med. Biol., 41 (1996) pp. 1973-1992.
Bouma et al, "Anthracycline antitumour agents", Pharmaceutisch Weekblad Scientific Edition, 8 (1986) pp. 109-133.
Haj et al, "New findings in the study on the intercalation of bisdaunorubicin and its monomeric analogues with naked and nucleus DNA", Chemico-Biological Interactions, 145 (2003) pp. 349-358.
Murali et al, "Synthesis of 4'-Epi-lodo-4'-Deoxy-Daunorubicin, a Potential Cancer Radiotherapeutic Agent", Bioorganic & Medicinal Chemistry Letters, 8 (1998) pp. 3419-3422.
Keizer et al, "Doxorubicin (Adriamycin): A Critical Review of Free Radical-Dependent Mechanisms of Cytotoxicity", Pharmac. Ther., vol. 47 (1990) pp. 219-231.
Blum et al, "A New Anticancer Drug with Significant Clinical Activity", Annals of Internal Medicine, 80 (1974) pp. 249-259.
Chabner et al, "Clinical Pharmacology of Cancer Chemotherapy", in "Cancer: Principals and Practice of Oncology," DiVita, Jr., et al, Eds., J.B. Lippincott Company, Philadelphia (1982) pp. 156-197.
Kim, "Liposomes as Carriers of Cancer Chemotheraphy", Drugs, 46 (4) (1993) pp. 618-638.
Ghirmai et al, "Synthesis and Radioiodination of Some Daunorubicin and Doxorubicin Derivatives," Carbohydrate Research, 340 (2005), pp. 15-24.
Allen, "Ligand-Targeted Therapeutics in Anticancer Therapy," Nature Reviews, Oct. 2002, vol. 2, pp. 750-763.
Milenc, et al., "Targeting of Radio-Isotopes for Cancer Therapy," Cancer Biology & Therapy 3:, Apr. 2004, pp. 361-370.
Ickenstein et al, Nuclear Medicine and Biology, 33:773-783 (2006).
Fondell et al, European Journal of Nuclear Medicine and Molecular Imaging, 37:114-123 (2010).
Olsufyeva et al, Synthesis and antitumor activity of new D-glactose-containing derivatives of doxorubicin, Carbohydrate Research, 338:1359-1367 (2003).
Medical Dictionary, 2nd Edition, lshiyaku Publishers Inc., 1996, pp. 1064 and 1221.

* cited by examiner

*Primary Examiner* — Anna Pagonakis
(74) *Attorney, Agent, or Firm* — Porter Wright Morris & Arthur LLP (57) ABSTRACT

Anthracycline derivatives are suitable for use in cancer therapy and diagnosis. These anthracycline derivatives can be radiolabelled and used as an imaging agent in cancer diagnosis. The radiolabelled anthracycline derivatives can also be used together with a drug delivery system, in particular including a two-step targeting strategy, for treating solid and disseminated tumors. These drug delivery system can advantageously be used for treatment and diagnosis of breast cancer.

9 Claims, 3 Drawing Sheets

DNA-binding of $^{125}$I-Compound 1

ANTHRACYCLINE DERIVATIVES

RELATED APPLICATIONS

The present application is a divisional application of U.S. application Ser. No. 11/578,159 filed Oct. 10, 2006 now abandoned, which is a 371 of PCT/SE2005/000596 filed Apr. 22, 2005.

FIELD OF THE INVENTION

The present invention relates to new anthracycline derivatives and their use in cancer therapy and cancer diagnosis.

BACKGROUND

Doxorubicin ($C_{27}H_{29}NO_{11}$; MW: 543.53), abbreviated as DOX, also known among other names as adriamycin, or adriablastine is an antibiotic and antineoplastic agent of the anthracycline family (see structure below). DOX was originally isolated from the aquatic bacterium *Streptomyces peucetius* var. *coesius* and since the early 1970s, anthracyclines, in particular doxorubicin and daunorubicin, and alkylating agents (cyclophosphamide, melphalan, etc.) are the most versatile and most frequently used chemotherapeutic agents in the clinic today [1]. Anthracyclines are amphipathic molecules consisting of a hydrophobic aglycone heterocycle with a quinone-hydrochinone functional group and a hydrophilic aminosugar moiety [2, 3].

Chemical Structure of Daunorubicin and Doxorubicin

Daunorubicin: $R^1 = CH_3$
Doxorubicin: $R^1 = CH_2OH$

Doxorubicin is used extensively in the treatment of bone and soft tissue sarcomas and carcinomas of the lung, breast, thyroid, bladder, ovary, testis, head, and neck [1, 4]. Doxorubicin is also used against leukemias and lymphomas but daunorubicin is the primarily treatment against acute leukemias. The overall response rates for doxorubicin is 45% for thyroid cancer, 41% for lymphomas, 33% for bladder carcinomas, 26% for sarcomas, 25% for ovarian carcinomas, 24% for leukemias [5].

Doxorubicin has multiple mechanisms of action but the main anti-tumour activity of doxorubicin and other anthracyclines stems from their ability to intercalate with DNA resulting in blockade of DNA-, RNA- and protein-synthesis. Anthracyclines also inhibit topoisomerase II and impair DNA repair [1, 5]. Because of their quinone-hydroquinone functional group, anthracyclines are thought to be involved in the generation of free radicals leading to DNA damage [2].

Anthracyclines bind specifically to cardiolipin, a phospholipid found in high concentrations in cardiac mitochondria and membranes of malignant cells, which may explain cardiotoxic side effects of doxorubicin [1]. Anthracyclines have narrow therapeutic indices, i.e. the administered dose has to be within narrow limits, since the drug has no effect if the dosage is too small and severe side effects can result if the dosage is too large. The acute dose-limiting toxicity of doxorubicin is bone-marrow suppression, leukopenia, and stomatitis occurring in 80% of treated patients. Other side effects include alopecia (100%), nausea and vomiting (20-55%), cardiac toxicity, i.e. supraventricular arrhythmias, heart block, ventricular tachycardia and even congestive heart failure in 1-10% of patients.

Previously, anthracycline derivatives have been disclosed by e.g. Pribe (2003) Chemico-Biological Interactions 145: 349-358, U.S. Pat. No. 4,948,880, U.S. Pat. No. 6,673,907, and WO00/56267. These derivatives have cytotoxic effect in cancer treatment.

Radionuclide therapy has a relatively small but important role in cancer therapy and is currently gaining increasing attention. Radionuclide therapy implements nuclear radiation to eradicate malignant cells. The radiation can be generated by stable nuclides e.g. $^{10}B$ and $^{157}Gd$ following neutron activation or by radioactive nuclides. The most commonly used therapeutic radionuclide especially against thyroid cancer is the intermediate-range (800 μm) β-emitter, $^{131}I$, but administration of $^{131}I$ causes considerable radiation damage in healthy tissue [6]. However, due to these side effects the therapeutic potential of short-range, low-energy Auger electron emitters, such as $^{125}I$, is getting progressively wider recognition. In order for it to be effective in anticancer treatment, $^{125}I$ has to be delivered directly and selectively into tumour cell nuclei since $^{125}I$ is not toxic unless it is within a few nanometers from the DNA [7]. $^{125}I$ therapy thus requires a method of specific nuclear delivery, which has previously been achieved using $^{125}I$-labelled nucleosides, oligonucleotides, steroid hormones and growth factors but a need for improvement has been recognized [7].

Murali D. and DeJesus. O, Bioorganic & Medicinal Chemistry letters 8 (1998) 3419-3422, describes a radiolabelled daunorubicin derivative having improved cytotoxic properties compared to doxorubicin. No results are presented in the article, and no continuation of this work has been published.

Targeted drug delivery via liposomes minimizes the dose-limiting side effects of conventional cancer chemotherapy such as bone marrow suppression, mucositis, cardiac-, neuro-, and nephro-toxicity [1] by encapsulating the cytotoxic agent into membrane bound vesicles (liposomes) and coupling tumour-specific antibodies to the liposome membrane (targeted liposomes). Targeted liposomes in the blood are actively and selectively taken up by tumour cells overexpressing the targeted surface marker. However, despite some progress, this strategy has so far not resulted in a major improvement in chemotherapy [8]. Thus, there is a great need for more potent therapeutic agents and treatment strategies.

SUMMARY OF THE INVENTION

The present invention relates to diagnostic and therapeutic agents possessing DNA-intercalating properties and to which nuclides can be coupled. The present invention further relates to drug delivery systems for these diagnostic or therapeutic agents and therapeutic and diagnostic methods using said agents or drug delivery systems. The present invention is intended for cancer diagnostics and therapy. The aim of the present invention is to deliver a nuclide specifically into tumour cell nuclei and thus to combine the benefits of radionuclide therapy, chemotherapy, and targeted liposomal drug delivery in a single two-step targeting approach that minimizes cytotoxic side effects in healthy tissue. Thus, the present invention provides a new therapeutic strategy with novel drugs, which are potentially more potent than previously known chemotherapeutic drugs.

Anthracyclines are potent anticancer drugs by themselves. In the present application, the inventors have synthesized amino-benzyl derivatives of daunorubicin (drug precursors), which have similar cytotoxicity profiles as the commercially successful anthracyclines doxorubicin and daunorubicin. When the present inventors iodinated the drug precursors with $^{125}$I, they obtained radiotherapeutic agents being more effective against cultured tumor cells, To protect healthy tissue and to deliver the radionuclide selectively into malignant cancer cells, the $^{125}$I-coupled daunorubicin derivatives can be encapsulated into targeted liposomes, which serve as specific drug delivery vehicles for tumor cells.

The results of the experiments described herein confirm that the therapeutic agents according to the present invention can successfully be encapsulated into targeted liposomes, and that the drugs are well retained under the experimental preparation and assay conditions. After incubation with tumour cells, the above-mentioned agents reach and bind to the cell nucleus with a similar affinity as that of doxorubicin. When bound to DNA, the radiotherapeutic agent causes DNA fragmentation, leading to a tumour cell growth inhibition of several orders of magnitudes higher than that caused by doxorubicin and daunorubicin, two of the most successful chemotherapeutic agents in the clinic today.

None of the drugs precursors or radiotherapeutic drugs according to the present invention have previously been described in the prior art.

According to one aspect of the invention, there is provided anthracycline derivatives that serve as precursor molecules for the radiotherapeutic agents, and which will henceforth be referred to as drug precursors. The drug precursors intercalate with DNA and possess cytostatic properties. The drug precursors can thus be used in cell- or tissue-targeted cancer therapy by themselves. The anthracycline derivatives (drug precursors) are disclosed herein.

According to a further aspect of the invention, there is provided radiotherapeutic drugs that can be used in cell- or tissue-targeted radiotherapy. The radiotherapeutic agents are generated from their precursors by linking the drug precursors to a nuclide or a chemical group containing a nuclide. Such a nuclide may be a radioactive nuclide, a stable nuclide, or a nuclide that can be activated by exposure to neutrons or photons, e.g. $^{10}$B (as part of a boron-rich cage-compound derivative such as the closo-carboranes o-, m- or p-$C_2H_{12}B_{10}$) and will henceforth be referred to as nuclides. The radiotherapeutic drugs are disclosed herein.

According to a still further aspect of the invention, the radiotherapeutic drug may also be used as an imaging tool for cancer diagnostics. The use as an imaging tool is disclosed herein.

According to a still further aspect of the invention, the drug precursor or radiotherapy drug may also be used as a DNA targeting agent, i.e. as a DNA-interacting agent as disclosed herein.

According to a still further aspect of the invention, there is also provided drug delivery systems. Said system preferably comprises a carrier capable of encapsulating the drug precursors or radiotherapeutic drugs (possessing DNA-interacting properties) and guide drugs specifically or preferentially to the targeted cell population. Consequently, cell- and tissue-damaging effects will affect preferentially targeted cells and tissues. Such drug delivery systems may involve single- or multiple-step targeting strategies. The DNA-intercalating properties of the drug precursors are the basis of the DNA-targeting step that directs their cytotoxic effects to the nucleus or, when the nuclide is coupled to the drug precursor, localizes the radioactivity emitted from the nuclide to the cell nucleus. This targeting step, which will henceforth be referred to as the DNA-targeting step, thus dramatically increases the therapeutic effect of the radiotherapeutic drugs and reduces damage to healthy cells and tissues.

To differentiate between malignant and healthy tissue, the radiotherapeutic drugs are directed towards cancer cells or tissues using a drug delivery system that exhibits a tumour-cell specific targeting agent at its surface as a cell-targeting step in a two-step targeting strategy, which will henceforth be referred to as the cell-targeting step. The drug carrier is capable of enclosing or binding the radiotherapy drug and directing its transport after systemic administration to and preferably across membranes of targeted cells. The cytotoxic and/or radiotoxic effect of the radiotherapeutic drugs will consequently be localized to the targeted cell population. The drug delivery system is disclosed herein.

According to a still further aspect of the invention, there is also provided a method of diagnosing or treating cancer, comprising administering said drug delivery systems including the precursor drug or radiotherapeutic drug to a patient in need thereof. In addition to its use as a treatment against solid tumours, the invention is also envisioned as a treatment against metastasizing tumour cells in systemic circulation after removal of the primary tumour. The treatment could be particularly beneficial against disseminated breast cancer, but also against disseminated ovarian, prostate and colorectal cancers.

Said therapeutic methods may also be used in combination with subsequent tumour radiation when the location of the tumour is known. Local radiotherapy can be achieved by using stable nuclides and activation by external irradiation with neutrons or photons.

The invention could also be an effective treatment against multi-drug resistant (MDR) tumours overexpressing P-glycoprotein (PGP), a membrane-bound efflux pump for xenobiotics. The radiotherapeutic drugs would in this case target and radiodamage P-glycoprotein, which is known to bind to anthracyclines. The therapeutic methods are disclosed herein.

DETAILED DESCRIPTION OF THE INVENTION

Drug derivatives described herein are intended for use as cancer therapeutics in the form of drug precursors or coupled to a nuclide as potent radiotherapeutic anti-cancer drugs or diagnostic imaging tools.

Their usefulness might however be compromised by their indiscriminate cytotoxicity to healthy tissue. This problem will be minimized by encapsulating drugs into liposomes, or alternative drug carriers, and selectively targeting the tumour cells by attaching tumour-specific targeting agents to the surface of liposomes or alternative drug carriers. Thus, the drug precursors or radiotherapeutic drugs are intended for use in combination with a two-step targeted drug delivery system as disclosed in U.S. Pat. No. 6,562,316. Such a drug delivery system comprises a carrier coupled to cell-targeting agent(s) to direct the drug delivery system in the cell-targeting step specifically to the targeted cell population or tissue. In the DNA-targeting step, encapsulated nuclides will be directed to the cell nucleus by their link to a molecule with DNA intercalating properties. The herein described drug precursors or radiotherapeutic drugs will serve as such DNA-targeting agents possessing DNA-intercalating properties.

The described two-step targeting system will minimize the cytotoxicity of nuclides, the drug precursors or radiotherapeutic drugs in healthy tissue. A further advantage of the two-step targeting system is that it has the potential for treatment of metastasized and/or multi-drug resistant tumour cells.

The drug carrier might be a molecule, an aggregate, or a particle able to bind or enclose pharmaceutically active agents, i.e. drug precursors or radiotherapeutic drugs. Liposomes are currently the preferred drug carriers, but polymeric drug carriers such as micro-gels, or lipid/polymer composite particles may be equally or better suited for certain applications.

The targeting agents for the cell-targeting step of the two-step targeting strategy bind selectively and with high affinity to the tumour cells. Ideally, tumour-specific targets are molecules that exist exclusively on tumour cell surfaces. However, a general tumour-specific cell marker that is present in all cancer cells but absent in normal cells has yet to be found and the similarities between the tumour cells and normal cells are by far outnumbered by their differences. There are, however a number of cell surface markers overexpressed specifically in certain tumour cells. EGF (epidermal growth factor) receptors are, for example, overexpressed in tumour cells of the brain, bladder, breast, and lung as compared to normal cells. EGF receptors in tumours can thus be targeted to attain high selectivity for EGF-conjugated radionuclides or stable nuclides. Monoclonal antibodies against target tumour cells have also been demonstrated to be effective for tumour-targeting.

The agent for the cell-targeting step is thus preferably chosen from a group comprising ligands, antibodies, or antibody fragments, and may also comprise epidermal growth factor (EGF) or a molecule that binds to a tumour-specific mutated EGF receptor.

The liposomal drug delivery system, the first-step targeting agent, and their respective preparations are described in the above-mentioned U.S. Pat. No. 6,562,316. The preparation of polymeric carriers or lipid/polymer carriers are not disclosed in present patent, but the person skilled in the art will easily obtain relevant preparation protocols from the literature.

Drug Precursors (DNA-Targeting Agent)

Anthracycline derivatives (drug precursors) used as DNA-targeting agents should possess DNA-interacting properties or electrostatic binding properties. DNA-intercalators are particularly suitable as DNA-targeting agents since intercalation of the molecule with DNA results by itself in therapeutic activity.

The general formula (I) of anthracycline derivatives according to the present invention is the following:

(I)

wherein:
R is either a double-bound oxygen atom, a hydroxyl group in both stereoisomeric forms, or
$R_1$ is either $CH_3$, $CH_2OH$,
$R_2$ is a Y—Ar—Z group, wherein:
Y is either a spacer molecule, such as —$(CH_2)_n$— or a polyethylene glycol chain having the formula —$(CH_2CH_2O)_n$—, where n is 1-8;
Ar is a conventional monocyclic aromatic group or stable aromatic boron cage compound, where the conventional aromatic residues comprise a substituent (such as a hydrogen atom) capable of being directly radiolabelled using electrophilic aromatic substitution or an activating group (e.g. a trialkylstannyl group such as a trimethylstannyl or tributylstannyl group), which can be exchanged for a radionuclide or which comprises a halogen (e.g. Br or I) such that the aromatic residue can undergo halogen-halogen exchange reactions; and
Z is optionally a chemical group that increases the hydrophilicity, such as a sugar group;
and salts thereof.

Examples of salts are salts like hydrochloride, hydrobromide, formates and other carboxylates.

The conventional monocyclic aromatic group is preferably a phenyl or pyridine group, and the stable aromatic boron cage compound is preferably a stable closo-carborane, such as $C_2H_{12}B_{10}$.

The present invention relates to stereoisomeric mixtures of said drug precursors (on which the radiotherapeutic drugs are based), as well as to the separate stereoisomers.

The agent for the DNA-targeting step must:
possess high affinity for the nuclear DNA,
possess properties that permit efficient loading into the carrier,
show minimal leakage (or release) at physiological pH and ionic strength when enclosed in (or bound to) the carrier,
possess properties that, following release from the carrier, enables the agent to reach and bind to nuclear DNA.

The drug precursors and radiotherapeutic drug according to the present invention exhibit these features.

Specific examples of the drug precursors are given below:

Synthesis of the Drug Precursors

The synthesis of the drug precursors follows standard procedures and can be performed by any person skilled in the art. The synthesis of the drug precursors is not part of the intended scope of protection.

Radiotherapeutic Drugs

When using the radiotherapeutic drugs according to the present invention, i.e. the drug precursors coupled to a nuclide, large amounts of nuclides will be delivered to the tumour cells and these nuclides will reach and bind to the nuclear DNA. Each radioactive decay will result in nuclear DNA damage. Thus, the radiotherapeutic drugs will be more potent than their drug precursors at the same concentration. The amount of DNA damage will be at least ten times higher when the radioactive nuclide is localized inside the cell nucleus as compared to the situation when the radioactive nuclide is outside the cell nucleus. Delivery of large amounts of radioactive nuclides to tumour cells may therefore expand the range of treatment from palliative to curative. If conventional cellular one-step (without the DNA-intercalation) targeting strategies are used only palliative treatments appear possible.

Every radionuclide has a distinct set of properties such as half-life, and type of emitted radiation. The invention allows to selectively choose the appropriate nuclide for the specific type of cancer or the specific clinical problem. The physical half-life of the chosen radionuclide has to be matched with the biological half-life of the drug precursor. It is therefore important that the emission characteristics of the radionuclide match the size and location of the particular tumour. High-energy beta emitters, such as $^{90}Y$, may be suitable for the treatment of large tumours. Other nuclides, such as $^{131}I$, emit low-energy beta particles and possess consequently a shorter range of radiation, which make them more suitable for smaller tumours or even single tumour cells. Auger electron emitters, such as $^{125}$I and $^{123}$I, emit particles that travel only about 1-2 μm and hence have to be located inside the cancer cell nucleus to cause DNA damage. The ranges of alpha particle emitters are typically between 50 and 70 μm and cause local deposition of a large amount of energy.

Radiohalogens have a wide range of physical half-lives and types of emitted radiation, which widens their range of application. The beta emitter, $^{131}$I is one of the most commonly used radionuclides in nuclide therapy. Positron emitting radiohalogens, such as $^{18}$F, $^{76}$Br, and $^{124}$I, can be used for diagnostic purposes in positron emission tomography (PET). They allow for radiation dosimetry of tissues and for monitoring changes of tumour volume via PET scans.

The radiohalogen $^{211}$At has a relatively short half-life (7.2 hours) and decays by α-particle emission. It is extremely cytotoxic and could therefore be an effective therapeutic agent if delivered specifically to the targeted cell population.

Auger electron emitters kill cells effectively when incorporated in the cell nucleus. $^{125}$I (half-life 60 days), $^{123}$I (half-life, 13.2 hours), and $^{77}$Br (half-life 56 hours) decay by electron capture followed by emission of Auger electrons. The radiotherapeutic drugs discussed in the present patent application are especially well suited for coupling to $^{125}$I. $^{125}$I is relatively inexpensive, widely commercially available, and its relatively long half-life is appropriate for in vitro applications. $^{123}$I might also be an attractive candidate for therapeutic use because of its short physical half-life and especially since it also emits γ-radiation in addition to Auger electrons, which allows for imaging.

Radionuclides with a short radiation range, $^{125}$I (Auger radiation) and $^{211}$At (alpha-particles) generate high local ionization densities and seem at present to be best suited for targeting single cells and will cause minimal damage to surrounding healthy cells or tissues.

Radiotherapeutic drugs may include stable nuclides, which can be activated by neutrons or photons. The stable nuclide $^{10}$B is not cytotoxic. However, if a $^{10}$B-enriched compound is selectively localized in tumour cells, cells can then externally be irradiated with non-toxic low-energy neutrons. These neutrons are captured by $^{10}$B atoms generating excited-state $^{11}$B atoms, which instantaneously disintegrates into two highly cytotoxic particles, α-particles and $^{7}Li^{3+}$ ions. The range of these ions in tissue is approximately 9 and 5 μm, respectively, which is close to one cell diameter. $^{157}$Gd can also be subjected to neutron activation. Other alternatives are stable iodine or bromine isotopes, which can be activated by photons. In addition, these isotopes can be combined with long-range β-emitting radionuclides, i.e. $^{131}$I, $^{32}$P, $^{67}$Cu, $^{90}$Y or $^{189}$Re producing cross-fire radiation suited for larger tumour cell aggregates. These neutron- or photon-activated nuclides can for example be stabilized using closed carboranes, i.e. boron rich cage-compounds such as the closo-carboranes o-, m- or p-$C_2H_{12}B_{10}$.

The radioactive nuclide in the radiotherapeutic drugs described in the present patent application is preferably $^{123-125}$I, $^{131}$I, $^{18}$F, $^{76-77}$Br, $^{211}$A, $^{90}$Y, $^{32}$P, $^{67}$Cu, or $^{189}$Re, and $^{125}$I is particularly preferred, and the stable nuclide is preferably $^{10}$B and $^{157}$Gd.

Radiolabeling of the Drug Precursors

All drug precursors for radioiodination contain an aromatic residue and are labeled with $^{125}$I using conventional methods such as the chloramine-T method. Radiolabeling was performed either by direct electrophilic substitution of an aromatic ring or by replacement of an activating group, such as a trialkylstannyl, e.g. a trimethylstannyl or tributylstannyl group, in the aromatic ring. These methods follow standard procedures and can be performed by any person skilled in the art.

EXAMPLES

To test if the drug precursors or radiotherapeutic drugs according to the present invention could be used in a drug delivery system, the following experiments were performed.

Example 1

Drug Retention in Liposomes

Preparation of Liposomes

Liposomes were composed of 1,2-distearoyl-sn-glycero-3-phosphatidyl-choline (DSPC), cholesterol, 1,2-distearoyl-sn-glycero-3-phosphatidyl-ethanolamine-N-[methoxy (poly-ethyleneglycol)-2000 (DSPE-PEG$_{2000}$) at a molar ratio of 57:40:3. Liposomes were prepared by the lipid film hydration method [9]. Briefly, cholesterol and lipids were dissolved in chloroform. The solvent was evaporated under a gentle stream of nitrogen gas and the lipid film was dried under vacuum overnight. The lipid film was hydrated with 300 mM citrate buffer (pH 4) for 1 h with intermediate vortex mixing at a lipid concentration of 20 mM at a temperature of 60° C. Liposomes were repetitively frozen in liquid nitrogen and thawed at a temperature of 60° C. five times before extrusion. Liposomes were extruded ten times through two stacked polycarbonate membranes filters (Whatman Inc. Nucleopore, Newton, Mass.) with a pore size of 100 nm at a room temperature using an Avanti Mini-extruder (Avanti Polar Lipids Inc., Alabaster, Ala.).

Drug Encapsulation

Compound 1 (3'-N-(4-hydroxy-3-iodobenzyl)-13-(R/S)-dihydrodaunorubicin, stereoisomeric mixture) and Compound 2 (3'-N-(4-Hydroxy-3-iodobenzyl)daunorubicin), structures are shown below, or doxorubicin (Sigma Aldrich, St. Louis, Mo., USA) were encapsulated into liposomes using the pH-gradient driven loading protocol by Mayer et al. The pH gradient across the liposome membrane was generated by exchanging the extravesicular 300 mM citrate buffer (pH 4) with 20 mM N-[2-hydroxyethyl]piperazine-N'-[2-ethanesulfonic acid] (HEPES) buffered 150 mM saline (HBS) (pH 7.5) on a Sephadex G-50 column. Doxorubicin was dissolved in HBS at a concentration of 1 mM. Compound 1 was dissolved at a concentration of 0.5 mM in 10% (wt/vol) sucrose solution. Compound 2 did not dissolve completely at a concentration of 0.5 mM in 10% (wt/vol) sucrose solution but dissolved when liposomes were added and drug was encapsulated into liposomes. A preheated drug solution was added to the liposomes at a 0.2 drug-to-lipid molar ratio. The mixture was incubated for 15 min at a temperature of 60° C. with intermittent mixing using a Vortex-apparatus resulting in 100% drug encapsulation.

Chemical Structures of Compounds 1 and 2

Figure 1:
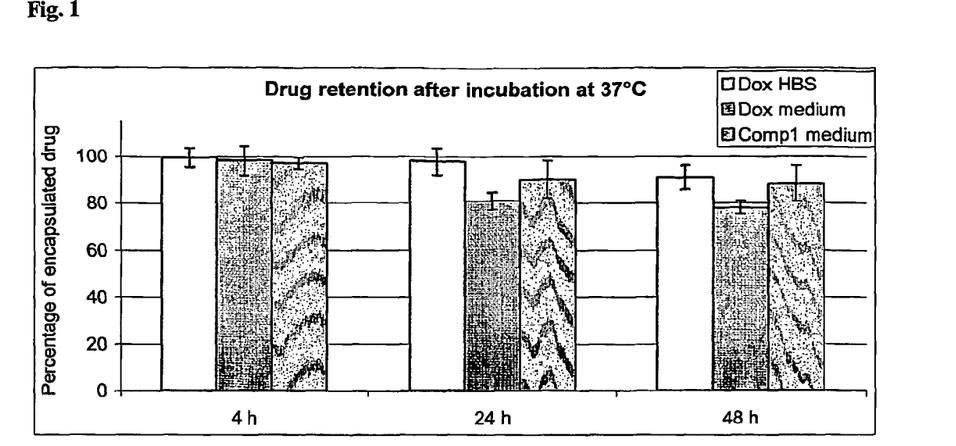
FIG. 1: Retention of doxorubicin in buffer or medium and Compound 1 in buffer at a temperature of 37° C.

Attachment of the Targeting Ligand Trastuzumab to Drug-Loaded Liposomes
a) Conjugation of $^{125}$I-Trastuzumab to DSPE-PEG$_{3400}$ The N-hydroxysuccinimidyl ester of 1,2-distearoyl-sn-glycero-3-phosphatidyl-ethanolamine-N-[methoxy (poly-ethyleneglycol)-3400 (NHS-DSPE-PEG$_{3400}$) was hydrated with $^{125}$I-trastuzumab solution at molar ratio of 0.1:6 at a temperature of 60° C. for 5 min Radiolabeled trastuzumab was used to trace liposomes. The concentration of NHS-DSPE-PEG$_{3400}$ was at approximately 0.2 mM. The mixture was incubated for 1 h at room temperature with stirring. Unbound trastuzumab was removed from $^{125}$I-trastuzumab-DSPE-PEG$_{3400}$ by gel filtration on a Sephacryl S-300 column with HBS (pH 7.4).
b) Transfer of $^{125}$I-trastuzumab-DSPE-PEG$_{3400}$ to Liposomes $^{125}$I-trastuzumab-DSPE-PEG$_{3400}$ was mixed with drug-loaded liposomes at a 1:33 molar ratio and a temperature of 60° C. for 1 h. Unincorporated $^{125}$I-trastuzumab-DSPE-PEG$_{3400}$ was removed from liposomes by gel filtration on a Sepharose CL-4B column with HBS (pH 7.4).
Determination of Drug Retention Liposomes were incubated at temperatures of 37° C. or 60° C. At selected time intervals, aliquots were withdrawn in triplicate and non-encapsulated drug was removed on a Sephadex G-50 mini-column with HBS (pH 7.5) in a centrifugal field of 680 g for 2 min The volume of the eluent was adjusted to 1 ml with HBS and 1 ml of 1% Triton X-100 solution was added. Samples were heated to a temperature of 90° C. and cooled down to room temperature. The fluorescence intensity of samples was determined at an excitation wavelength of 468 nm and an emission wavelength of 589 nm. The percentage of encapsulated drug after incubation was determined relative to the amount of encapsulated drug before incubation.
Cryogenic Transmission Electron Microscopy (Cryo-TEM) of the Loaded Lioposomes In brief, liposome samples were transferred on to a copper grid coated with a perforated polymer film in a custom-build environmental chamber at controlled temperature (25° C.) and humidity conditions to minimize water evaporation. Excess sample was removed by aspiration onto a filter paper. Thin (10-500 nm) sample films were vitrified by submersion in liquid ethane at a temperature of −165° C. and transferred under nitrogen atmosphere at a temperature of −165° C. into a Zeiss EM 920 A transmission electron microscope (Carl Zeiss Inc., Oberkochen, Germany). Samples were exposed to an electron density of 5-15 e$^-$/Å$^2$ and images were taken in zero-loss bright field mode with an acceleration voltage of 80 kV.
Results and Discussion Approximately 80% of doxorubicin and more than 90% of Compound 1 remained encapsulated in liposomes when incubated in medium at a temperature of 37° C. for 24 h (FIG. 1). These results show that under the described conditions for liposome preparation and cell culture, doxorubicin and Compound 1 will not be significantly released from liposomes.

Figure 2:
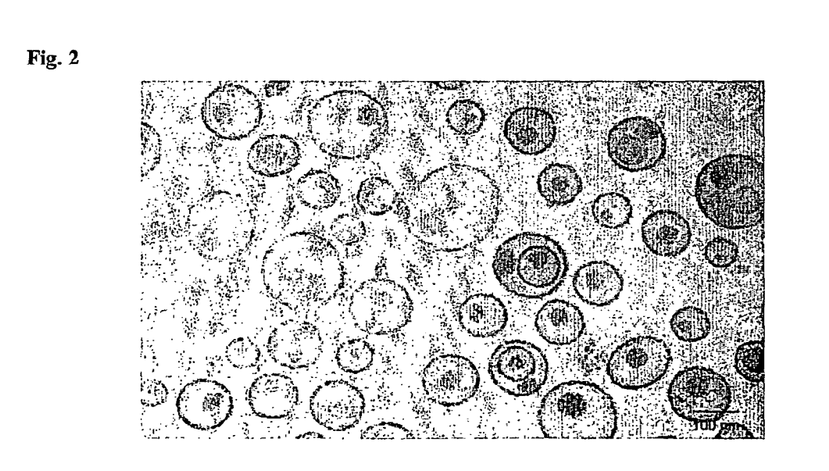
FIG. 2: Cryo-transmission microscopy image of liposomes loaded with Compound 1. The spheres represent liposomes and the spots inside the liposomes represent crystalline Compound 1.

The cryo-TEM image of liposomes containing $^{125}$I-trastuzumab-DSPE-PEG$_{3400}$ and loaded with Compound 1 (FIG. 2) confirms that Compound 1 is in a crystalline state inside the liposomes.

Example 2

DNA-Binding

Example 2a

Cell Culture

Human cultured tumour cells overexpressing were grown as monolayer cultures using Ham's F-10 medium (Biochrom AG, Berlin, Germany) containing 10% fetal calf serum, glutamine (2 mM), streptomycin (100 μg/ml), and penicillin (100 IU/ml) at a temperature of 37° C. in a humidified 5% CO$_2$ incubator.
DNA-Binding Cultured human tumour A431 cells (squamous carcinoma) were grown on glass slides, cooled to a temperature of 4° C., and washed with phosphate buffer. Cells were inactivated in methanol for 15 minutes at a temperature of −20° C. and then quickly washed at a temperature of 4° C. with phosphate buffer. Cells were thereafter permealised by acetone treatment for 10 seconds at a temperature of 4° C. After drying cells were incubated with $^{125}$I-Compound 1 at room temperature for one hour, washed, and analyzed for radioactivity using a gamma counter (1480 Wallac Wizard, Perkin Elmer, Wellesley, Mass., USA). In addition, cells were inspected by fluorescence microscopy.
Results and Discussion When cultured permealised human tumour A431 cells (squamous carcinoma) were incubated with $^{125}$I-Compound 1 at room temperature for one hour, the specific radioactivity of Compound 1 bound to cells was determined at 21.2±3.7× 10$^3$ cpm/10$^5$ cells after background subtraction. Binding could be blocked by using excess of doxorubicin.

Fluorescence microscopy revealed that Compound 1 was bound to the cell nucleus and not located inside the cytoplasm. Fluorescence microscopy experiments were repeated with similar results using human bladder cancer T24 and human glioma U343 cells.

Example 2b

Agarose Plugs

InCert agarose (BioWhittaker Molecular Applications, Rockland, Me.) was dissolved in serum free medium to a final concentration of 1%. 1 ml agarose solution was mixed with $1.5 \times 10^6$ U-343 cells and 20 µl plugs were cast in plastic moulds and cooled for 30 min at a temperature of 4° C. Plugs were submerged in lysis buffer (1 mg/ml Proteinase K, 2% Sarcosyl in 10 ml 0.5 M $Na_3$-EDTA, pH 8.0) at a temperature of 50° C. over night to obtain pure DNA. After lysis, the plugs were washed twice with 0.5 M $Na_3$-EDTA to remove cell debris. Plugs were stored at a temperature of 4° C. in 0.5 M $Na_3$-EDTA. Plugs without DNA served as controls. Agarose plugs were incubated in duplicates for 3 h on ice with 600 µl solution containing $^{125}$I-Compound 1. Control plugs contained excess amounts of doxorubicin at a concentration of $3 \times 10^{-5}$M. The final concentration of $^{125}$I-Compound 1 was $4 \times 10^{-7}$ M (in $dH_2O$). After incubation and thorough rinsing on ice the radioactivity remaining in plugs was determined using the gamma counter.

Autoradiography

SKBR-3 cultured breast cancer cells were incubated with $^{125}$I-Compound 1 for 1 h at a temperature of 37° C. at a concentration of 0.1 µg/ml culture media (0.3 kBq/ng). After incubation the cells were washed 6 times with serum free media and detached with 1 ml of trypsin/EDTA (0.25%/0.02% in PBS, Biochrome, Berlin, Germany) for 10 minutes. Cells were re-suspended with 14 ml culture media and transferred to centrifuge tubes. Cells were centrifuged for 5 min at 1200 rpm to get a cell pellet. The cell pellets were fixed with formalin buffer (0.01 M phosphate buffered formaldehyde (4%), Histolab Products AB, Göteborg, Sweden) for one week in 4° C. Thereafter pellets were dehydrated by following procedure: 2×15 min 70% EtOH, 30 min 90% EtOH, 2×15 min 95% EtOH, 2×15 min 99% EtOH and 3×20 min Historesin infiltration solution (Leica Instruments Gmbh, Heidelberg, Germany). After embedding in Historesin with activator over night 4 µm sections of the pellets were cut and transferred to slides. Slides were dipped into Kodak NTB photo emulsion (Eastman Kodak Company, Rochester, N.Y., USA) in darkness and dried before storage in 4° C. for 3 days. The slides were developed using Kodak D19 solution for 3 min, thereafter transferred to 0.1% acetic acid for 10 sec and fixed using Kodak fixer for 5 min, all in darkness. After extensive washing with water, cell nuclei were stained with Mayer Hematoxylin (Histolab Products AB, Göteborg, Sweden) for 3 min Before mounting with Pertex (Histolab Products AB, Göteborg, Sweden) slides were washed with water for 5 min and let to dry in air. Cells were inspected in microscope and images were captured of representative cells.

Results and Discussion

Figure 3:
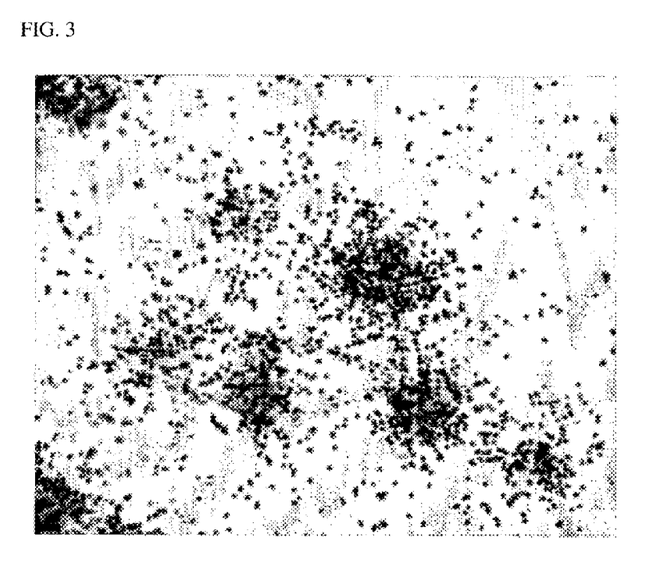
FIG. 3: Autoradiography of $^{125}$I-Compound 1 after 1 h of incubation at 37° C. with tumour cells.

Binding of Compound 1 to the cell nucleus could be confirmed by the autoradiography of $^{125}$I-Compound 1 (FIG. 3) since the staining pattern of $^{125}$I is co-localized with the Hematoxylin-stained cell nuclei.

Figure 4:
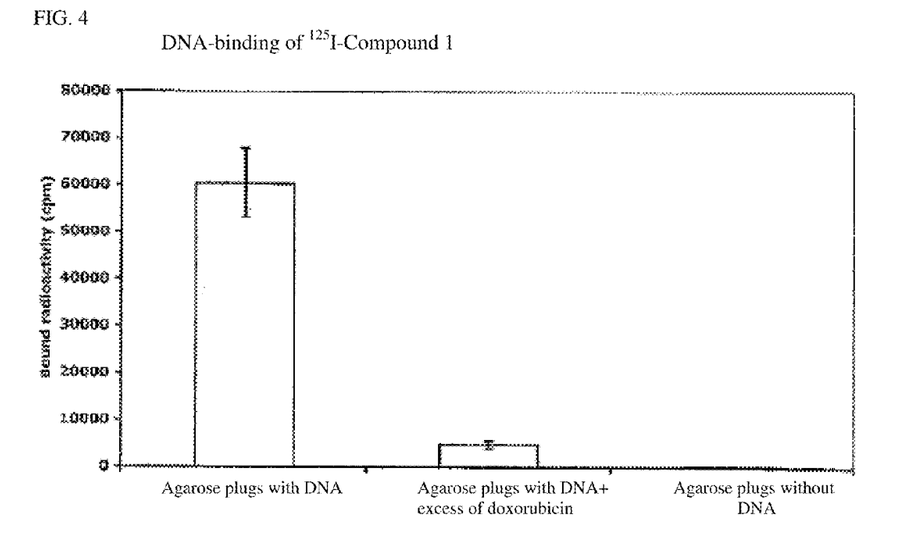
FIG. 4: Binding of $^{125}$I-Compound 1 to free DNA after 2.5 h incubation on ice.

When agarose plugs containing U-343 cellular DNA were incubated for 3 h on ice with $^{125}$I-Compound 1 solution, $^{125}$I-Compound 1 accumulated in the agarose plugs. Accumulation and thus binding of $^{125}$I-Compound 1 to DNA could be blocked by excess amounts of doxorubicin. Results confirm the affinity of Compound 1 to DNA. The fact that binding of $^{125}$I-Compound 1 to DNA could be displaced by doxorubicin (FIG. 4) suggests that both Compound 1 and doxorubicin occupy the same DNA binding sites.

Example 2c

Pulsed-Field Gel Electrophoresis (PFGE)

To investigate the efficiency of $^{125}$I-Compound 1 to induce DNA damage, the induction of double strand breaks (dsb) was analyzed on pulsed-field gel electrophoresis (PFGE, Pharmacia Biotech, Uppsala, Sweden). Agarose-plugs were incubated with $^{125}$I-Compound 1 as described above. After washing, plugs were maintained at a temperature of 4° C. for 8 days. Plugs were then loaded in a 0.8% (w/v) agarose gel (Seakem Gold agarose powder, Cambrex Bio Science Rockland Inc., Rockland, Me., USA). DNA-fragmentation was analyzed for 45 h pulse field gel electrophoresis at 2 V/cm according to the following protocol: 10 min pulses (i.e. the field is pulsed every 10 minutes) for 3 h, 20 min pulses for 5 h 20 min, 30 min pulses for 8 h, 40 min pulses for 9 h 20 min and 1 h pulses for 20 h. After the gel was run it was stained with ethidium bromide (0.5 µg/ml) for 8 h then destained in $dH_2O$ over night. As molecular weight marker, a *Scizosaccharomyces pombe*, Megabase DNA standard (Cambrex Bio Science Rockland Inc., Rockland, Me., USA) was used. Each lane was cut in 2 blocks, corresponding to DNA fragments having a size being equal to or less than 5.7 Mbp and equal to or greater than 5.7 Mbp, respectively. Each block was put in a vial and the radioactivity was measured in the previously mentioned automated gamma counter. The fraction of DNA smaller than 5.7 Mbp was determined and then used for the calculations with the Blöcher-formula:

$$F_{<k} = 1 - e^{-rk/n}(1 + rk/n (Int\ J\ Rad\ Biol\ 57, 7\text{-}12, 1990)$$

$F_{<k}$ is the fraction of DNA smaller than k base pairs, r is the average number of dsb/chromosome and n is the total number of base pairs in one chromosome of mean size. k=In this assay 5.7 Mbp was used; n=130 Mbp for the average human chromosome.

To obtain the number of double-strand breaks (r) the formula has to be solved numerically.

Results and Discussion

Figure 5:
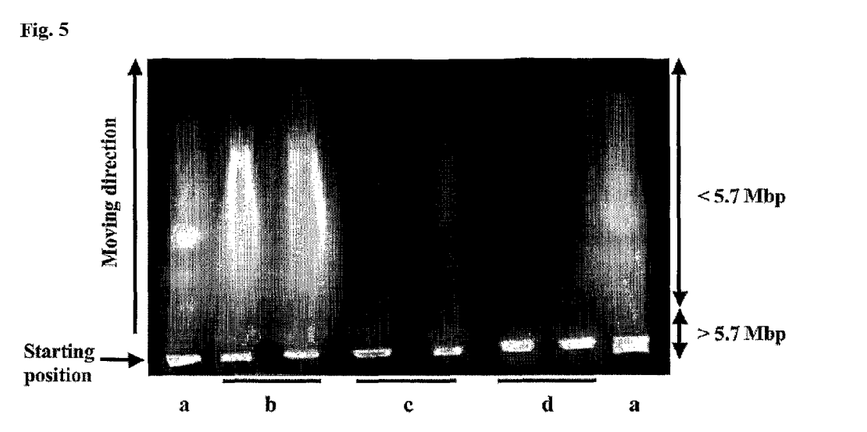
FIG. 5: DNA fragmentation after $^{125}$I-Compound 1-binding in an agarose gel loaded with plugs containing U-343MGaCl2:6 glioma cell DNA. In the figure, a) represents molecular weight marker (*Scizosaccharomyces pombe*, Megabase DNA standard), b) DNA incubated with $^{125}$I-Compound 1, c) DNA incubated with $^{125}$I-Compound 1 and excess of doxorubicin, and d) controls with DNA incubated without $^{125}$I-Compound 1.

The number of double-strand breaks (dsb) following incubation of $^{125}$I-Compound 1 with glioma cell DNA (FIG. 5) was determined at approximately 0.4 dsb/decay. Thus, when coupled to Compound 1, $^{125}$I is positioned close enough to DNA to cause DNA fragmentation, since $^{125}$I not bound to DNA would not lead to DNA fragmentation. As a comparison, the use of $^{125}$I-labeled DNA-precursor molecules, which results in direct incorporation of the nuclide into the DNA strand, gives a dsb value of approximately 1 dsb/decay. The difference in dsb values is relatively little, which indicates that the nuclide must have come within a very short distance from the DNA (in order for the radiation to have that effect) and that DNA-intercalation has occurred.

Example 2d

Type 1 calf thymus DNA sodium salt (Sigma-Aldrich Co., St Louis, M.O., USA) was hydrated in BPES buffer (6 mM $Na_2HPO_4$, 2 mM $NaH_2PO_4$, 1 mM EDTA, 185 mM NaCl, pH 7) at a concentration of approximately 2 mg/ml and sonicated at approximately 8 µA in a MSE Soniprep 150 ultrasonic disintegrator (Integrated Services TCP Inc., Palisades Park, N.J., USA) for 30 min in a water bath on ice. The sample was then dialyzed for 48 h against BPES using Slide-A-Lyzer® dialysis cassettes (10,000 MWCO) (Pierce, Rockford, Ill., USA). The final DNA concentration was determined spectrophotometrically on a HP8453 spectrophotometer (Hewlett-Packard Company Houston Tex., USA) at a wavelength of 260 nm using an extinction coefficient of 12,824 M $(bp)^{-1}$ $cm^{-1}$.

Fluorescence titration experiments were performed on a SPEX 1680 Fluorolog spectrofluorometer (SPEX Industries Inc., Edison, N.J., USA) at room temperature with $\lambda_{ex}$=480 nm (slid width 2.5 mm) and $\lambda_{em}$=592 nm (slid width 2.5 mm). The initial free drug concentration was 1 μM. The concentration of free drug ($C_f$(M)) was calculated by determining the fluorescence intensity ratio of investigated compounds in the absence ($I_0$) and presence of DNA (I) according to:

$$C_f = C_T(I/I_0 - P)/(1-P) \text{ (Biopolymers 6, 1225-1235, 1968)}$$

where $C_T$ (M) is the initial drug concentration, and P is the ratio between the observed quantum yield of fluorescence intensity of the fully bound drug ($I_{min}$) and that of the free drug (P=$I_{min}/I_0$). The concentration of bound drug was calculated by the difference between $C_T$ and $C_f$. Binding constants ($K_i$) and exclusion parameters (n) were calculated by plotting r/$C_f$ versus r (Scatchard plot), where r is the number of moles of bound drug per mol DNA base pairs. Theoretical curves for the neighbor exclusion model were calculated by using the algorithm:

$$r/C_f = K_i(1-nr)[(1-nr)/[1-(n-1)r]]^{n-1} \text{ (J. Mol. Biol. 86, 469-489, 1974)}$$

where $K_i$ ($M^{-1}$) is the intrinsic binding constant and n (base pairs) is the exclusion parameter. The parameters $K_i$ and n were varied to generate theoretical curves that closest fitted the experimental data.

Table 1 (below) shows binding constants ($K_i$) and exclusion parameters (n) of daunorubicin, doxorubicin, Compound 1 and Compound 2 to calf thymus DNA (CT DNA). Values in parentheses indicate the standard error of mean values (SEM) (n=3). $^a$=p<0.05 versus daunorubicin. $^b$=p<0.05 versus Compound 2. Differences between the mean values were tested by one way analysis of variance followed by the Student Newman-Keuls test.

Literature Values

Daunorubicin $K_i$: 0.7×$10^6$ $M^{-1}$±0.07, n: 3.5 base pairs±0.35 (Chaires, et al. (1982) *Biochemistry* 21, 3933-3940). Doxorubicin 3.3×$10^6$ $M^{-1}$, n: 3.8 base pairs (Messori et al. (2001) *Bioorg. Med. Chem.* 9, 1815-1825).

TABLE 1

Binding constants and exclusion parameters of doxorubicin, daunorubicin, Compound 1, and Compound 2.

| Drug | $K_i$ (Ki × $10^6$ $M^{-1}$) | n (base pairs) |
|---|---|---|
| Daunorubicin | 0.7 (0.05) | 3.6 (0.17) |
| Doxorubicin | 3.2 $^a$ (0.64) | 3.9 (0.23) |
| Compound 1 | 3.3 $^a$ (0.11) | 3.4 (0.21) |
| Compound 2 | 3.0 $^a$ (0.65) | 3.7 (0.31) |

Results and Discussion

The similarity of CT DNA binding constants and exclusion parameters of Compound 1 and Compound 2 to those of doxorubicin, confirms that the derivatisation of daunorubicin did not cause loss of DNA-binding properties (Table 1). On the contrary, the binding constants of Compound 1, and Compound 2 were higher than that of the parent compound, daunorubicin?.

Example 3

Toxicity

Growth curves [125]I-Compound 1, Compound 1, doxorubicin, or daunorubicin were dissolved in culture media to a concentration of 0.5 ng/ml. The specific activity of [125]I-Compound 1 was 100 kBq/ng. SKBR-3 cells were incubated with drug in 60 mm plastic Petri dishes as triplicates, for 2.5 h. Control-cells were incubated with ordinary culture medium. After incubation, the medium was removed from all dishes and cells were washed six times with serum-free medium. Cells were detached from dishes by adding 0.5 ml of trypsin/EDTA for 10 min at a temperature of 37° C. After re-suspension in 1 ml of culture media cells were counted using a coulter counter (Z2 Coulter Counter, Beckman Coulter) and sub-cultivated to $10^5$ cells to generate growth curves. Growth curves were corrected for loss of cells at each sub-cultivation.

Results and Discussion

Figure 6:
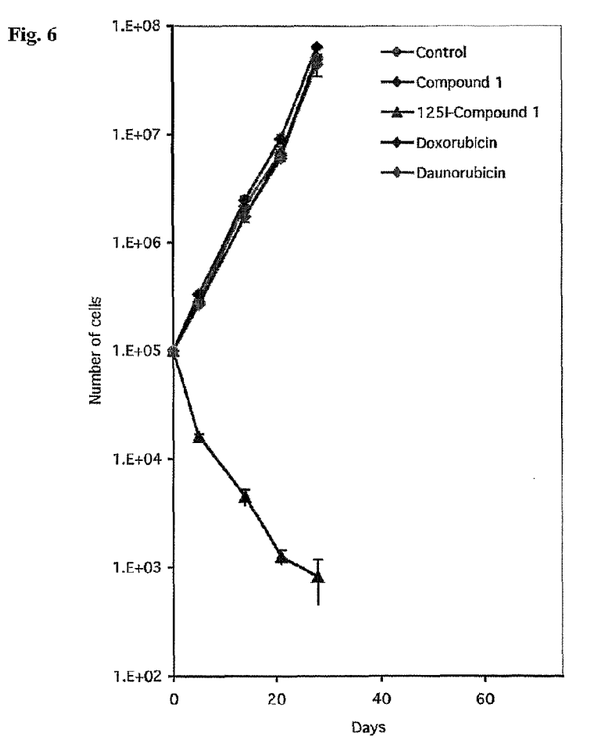
FIG. 6: Growth curves of tumour cells treated with 0.5 ng/ml of doxorubicin, daunorubicin, Compound 1, or $^{125}$I-Compound 1.

Growth curves of cultured SKBR-3 cell monolayers revealed that the cytotoxic effect of [125]I-Compound 1 at a concentration of as little as 0.5 ng/ml was greater by several orders of magnitudes as compared to that after incubation with Compound 1, doxorubicin, or daunorubicin (FIG. 6). Neither of the latter compounds had any significant cytotoxic effect. Hence, the cytotoxic effect displayed by [125]I-Compound 1 is solely caused by the nuclide $^{125}$I attached to Compound 1.

REFERENCES

[1] B. A. Chabner, C. E. Meyers (1982) in Cancer: Principles and practice of oncology (DeVita Jr. V. T., S. Hellman and S. A. Rosenberg, eds.), pp. 156-197, J. B. Lippincott Company, Philadelphia, Toronto.

[2] H. G. Keizer, H. M. Pinedo, G. J. Schuurhuis, H. Joenje, Doxorubicin (adriamycin): A critical review of free radical-dependent mechanisms of cytotoxicity, Pharmaceutics and Therapeutics 47 (1990) 219-231.

[3] J. Bouma, J. H. Beijnen, A. Butt, W. J. M. Underberg, Anthracycline antitumour agents, Pharmaceutisch Weekblad Scientific Edition 8 (1986) 109-133.

[4] C. P. Association, Compendium of pharmaceuticals and specialities, Vol. 13, CK Productions Toronto, 1995.

[5] R. H. Blum, S. K. Carter, Adriamycin. A new anticancer drug with significant clinical activity, Ann Intern Med 80 (1974) 249-59.

[6] M. N. Gaze, The current status of targeted radiotherapy in clinical practice, Phys Med Biol 41 (1996) 1895-903.

[7] J. A. O'Donoghue, T. E. Wheldon, Targeted radiotherapy using auger electron emitters, Phys Med Biol 41 (1996) 1973-92.

[8] S. Kim, Liposomes as carriers of cancer chemotherapy. Current status and future prospects, Drugs 46 (1993) 618-38.

[9] (M. J. Hope, M. B. Bally, G. Webb, and P. R. Cullis (1985) Biochim Biophys. Acta 812: 55-65).

What is claimed is:
1. An anthracycline derivative of the general formula I, wherein:
R is either a double-bound oxygen atom or a hydroxyl group in both stereoisomeric forms,
$R_1$ is $CH_3$ or $CH_2OH$, and
$R_2$ is a Y—Ar—Z group, wherein:
Y is —$(CH_2)_n$— or a polyethylene glycol chain of the formula —$(CH_2CH_2O)_n$—, where n is 1-8;
Ar is a monocyclic aromatic group substituted with a radioactive nuclide selected from the group consisting of $^{123-125}I$, $^{131}I$, $^{18}F$, $^{76-77}Br$, $^{211}At$, $^{90}Y$, $^{32}P$, $^{67}Cu$, and $^{189}Re$ or with a stable nuclide that is selected from the group consisting of $^{10}B$ and $^{157}Gd$; and
Z is a hydroxyl group or a sugar group;
and salts thereof.

2. The anthracycline derivative according to claim 1 wherein Y is —$(CH_2)_n$—, where n is 1-8.

3. An anthracycline derivative according to claim 1 selected from the group consisting of wherein X is a radioactive nuclide selected from the group consisting of $^{123-125}I$, $^{131}I$, $^{18}F$, $^{76-77}Br$, $^{211}At$, $^{90}Y$, $^{32}P$, $^{67}Cu$, and $^{189}Re$ or with a stable nuclide that is selected from the group consisting of $^{10}B$ and $^{157}Gd$.

4. The anthracycline derivative according to claim 1, where Ar is a monocyclic aromatic group substituted with the radioactive nuclide $^{125}I$ or $^{211}At$.

5. A drug delivery system comprising (a) a carrier capable of enclosing or binding a pharmaceutically active agent, and (b) one or more anthracycline derivatives according to claim 1 wherein the carrier is a lipid carrier, a polymeric carrier or a lipid/polymer composite particle.

6. The drug delivery system according to claim 5, wherein the lipid carrier is a liposome and the polymeric carrier is a microgel.

7. The drug delivery system according to claim 5, wherein the drug delivery system includes a two-step targeting system comprising:
   (a) a cell-targeting agent provided on the carrier to target specific cells or tissue, and
   (b) a DNA-interacting agent provided inside or bound to the carrier in order to target the radioactive nuclide to the cell nucleus.

8. The drug delivery system according to claim 5 wherein the cell targeting agent is selected from the group consisting of ligands, antibodies, and antibody fragments.

9. A method for treating breast cancer, comprising the steps of administering to a subject in need thereof a therapeutically efficient amount of the drug delivery system according to claim 5, and subsequently optionally irradiating a tumour area when a tumour has been located.

* * * * *